(12) United States Patent
Oza et al.

(10) Patent No.: US 11,564,278 B2
(45) Date of Patent: Jan. 24, 2023

(54) METHOD AND SYSTEM FOR MANAGING COMMUNICATION BETWEEN EXTERNAL AND IMPLANTABLE DEVICES

(71) Applicant: Pacesetter, Inc., Sylmar, CA (US)

(72) Inventors: Taral Oza, San Jose, CA (US); Gabriel A. Mouchawar, Valencia, CA (US); Samir Shah, Valencia, CA (US); Tejpal Singh, Stevenson Ranch, CA (US); John Stockton, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/541,783

(22) Filed: Dec. 3, 2021

(65) Prior Publication Data

US 2022/0095408 A1 Mar. 24, 2022

Related U.S. Application Data

(62) Division of application No. 16/682,639, filed on Nov. 13, 2019, now Pat. No. 11,224,087, which is a
(Continued)

(51) Int. Cl.
*H04W 76/23* (2018.01)
*H04W 24/08* (2009.01)
(Continued)

(52) U.S. Cl.
CPC ........ *H04W 76/23* (2018.02); *A61N 1/37252* (2013.01); *G16H 20/30* (2018.01);
(Continued)

(58) Field of Classification Search
None
See application file for complete search history.

(56) References Cited

U.S. PATENT DOCUMENTS

| 5,971,921 A | 10/1999 | Timbel |
| 6,804,558 B2 | 10/2004 | Haller et al. |

(Continued)

FOREIGN PATENT DOCUMENTS

| EP | 001961364 A1 | 8/2008 |
| GB | 002388194 A | 11/2003 |

(Continued)

OTHER PUBLICATIONS

International Search Report and Written Opinion for corresponding PCT Application No. PCT/US2018/031361 dated Oct. 16, 2018 (19 pages).

*Primary Examiner* — Pablo N Tran
(74) *Attorney, Agent, or Firm* — The Small Patent Law Group LLC; Dean D. Small

(57) ABSTRACT

Systems and methods for managing bi-directional communication between an external device (ED) and an implantable medical device (IMD) are provided. The method comprises receiving an active ED configuration and a request for communications parameters to be used with the active ED configuration. The method further comprises identifying a pre-existing configuration, from a collection of pre-existing configurations that match the active ED configuration, the collection of pre-existing configurations having an associated collection of predefined parameter sets. The method further determines a resultant parameter set from the collection of predefined parameter sets based on the pre-existing configuration identified and returns the resultant parameter set in connection with the request, the resultant parameter set to be utilized by the ED for bi-directional communication with the IMD.

20 Claims, 7 Drawing Sheets

Related U.S. Application Data division of application No. 15/971,836, filed on May 4, 2018, now Pat. No. 10,517,134.

(60) Provisional application No. 62/504,595, filed on May 11, 2017.

(51) Int. Cl.

| | | |
|---|---|---|
| *A61N 1/39* | (2006.01) | |
| *A61N 1/362* | (2006.01) | |
| *H04W 76/10* | (2018.01) | |
| *G16H 40/63* | (2018.01) | |
| *A61N 1/372* | (2006.01) | |
| *G16H 40/40* | (2018.01) | |
| *G16H 40/67* | (2018.01) | |
| *G16H 20/30* | (2018.01) | |
| *H04W 4/80* | (2018.01) | |

(52) U.S. Cl.
CPC ............. *G16H 40/40* (2018.01); *G16H 40/63* (2018.01); *G16H 40/67* (2018.01); *H04W 24/08* (2013.01); *H04W 76/10* (2018.02); *H04W 4/80* (2018.02)

(56) References Cited

U.S. PATENT DOCUMENTS

| | | |
|---|---|---|
| 6,957,107 B2 | 10/2005 | Rogers et al. |
| 7,072,718 B2 | 7/2006 | Von Arx et al. |
| 7,164,886 B2 | 1/2007 | Mowery et al. |
| 7,289,029 B2 | 10/2007 | Medema et al. |
| 7,672,731 B2 | 3/2010 | Dublin et al. |
| 8,000,532 B2 | 8/2011 | Van Hove et al. |
| 8,103,471 B2 | 1/2012 | Hayter |
| 8,239,166 B2 | 8/2012 | Hayter et al. |
| 8,993,331 B2 | 3/2015 | Nekoomaram et al. |
| 9,550,031 B2 | 1/2017 | Van Sickle et al. |
| 9,717,925 B2 | 8/2017 | King et al. |
| 10,050,700 B2 | 8/2018 | Ludwig et al. |
| 10,159,433 B2 | 12/2018 | Mazza et al. |
| 10,182,336 B1 * | 1/2019 | Stockton ............. A61N 1/37252 |
| 10,357,159 B2 | 7/2019 | Schmidt et al. |
| 10,388,411 B1 | 8/2019 | Dicks et al. |
| 10,560,135 B1 | 2/2020 | Dicks et al. |
| 10,561,330 B2 | 2/2020 | Kharam et al. |
| 10,762,991 B2 * | 9/2020 | Witt ....................... G16H 10/60 |
| 2007/0195789 A1 * | 8/2007 | Yao ....................... H04W 28/02 |
| | | 370/395.21 |
| 2008/0288024 A1 | 11/2008 | Abrahamson et al. |
| 2009/0063187 A1 | 3/2009 | Johnson et al. |
| 2009/0063193 A1 * | 3/2009 | Barton ................... A61B 5/349 |
| | | 340/539.11 |
| 2010/0111095 A1 | 5/2010 | Trossell et al. |
| 2010/0225468 A1 | 9/2010 | Sievert et al. |
| 2012/0057518 A1 | 3/2012 | Herrala et al. |
| 2016/0183276 A1 | 6/2016 | Marinier et al. |
| 2018/0243573 A1 * | 8/2018 | Yoder .................. A61B 5/0031 |
| 2018/0368197 A1 * | 12/2018 | Zeilingold ............ H04W 48/18 |
| 2020/0066415 A1 * | 2/2020 | Hettig ................... G16H 50/30 |
| 2022/0104293 A1 * | 3/2022 | Doudian ............... H04W 76/15 |

FOREIGN PATENT DOCUMENTS

| | | |
|---|---|---|
| KR | 20120063917 A | 6/2012 |
| WO | 0152934 A1 | 7/2001 |
| WO | 003039361 A1 | 5/2003 |
| WO | 2006119097 A1 | 11/2006 |
| WO | 2006147254 A1 | 12/2008 |
| WO | 2015063650 A1 | 5/2015 |

* cited by examiner

METHOD AND SYSTEM FOR MANAGING COMMUNICATION BETWEEN EXTERNAL AND IMPLANTABLE DEVICES

CROSS REFERENCE TO RELATED APPLICATIONS

This application is a divisional of U.S. patent application Ser. No. 16/682,639 filed Nov. 13, 2019, which is a divisional of U.S. patent application Ser. No. 15/971,836, filed May 4, 2018 (now U.S. Pat. No. 10,517,134, issued Dec. 24, 2019, which claims benefit of U.S. Provisional Application Ser. No. 62/504,595, filed May 11, 2017, the complete subject matter of which are expressly incorporated herein by reference in their entirety.

BACKGROUND OF THE INVENTION

Embodiments of the present disclosure generally relate to systems and methods for bi-directional communication with an implantable medical device (IMD), and more particularly between an external device and an IMD.

An IMD is a medical device that is configured to be implanted within a patient anatomy and includes one or more electrodes that either receive or deliver voltage, current or other electromagnetic pulses (generally "energy") from or to an organ or tissue for diagnostic or therapeutic purposes. In general, IMDs include a battery, a pulse generator and/or a microprocessor that is configured to perform diagnostic monitoring, manage communication with an external device, control patient therapy and the like. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Recently, it has been proposed to communicate with IMDs using commercial protocols, such as Bluetooth Low Energy (BLE), which are compatible with commercial wireless devices such as tablet computers, smartphones, and the like. It has been proposed to enable numerous types of mobile devices to communicate wirelessly with IMDs through software applications loaded on the mobile devices. For example, an application may be offered online for download to a smartphone, tablet device or other portable device, where the application enables the mobile device to communicate with one or more types of IMDs. Once the application is downloaded, the communications protocol (e.g., BLE) requires fine tuning with different parameter values for each type of mobile device. However, a challenge that remains for recent proposals is to accommodate a large number of mobile device configurations and find preferred BLE parameters for a large number of mobile device configurations.

BRIEF SUMMARY

In accordance with an embodiment herein, a computer implemented method for managing bi-directional communication between an external device (ED) and an implantable medical device, the method comprising receiving an active ED configuration and a request for communications parameters to be used with the active ED configuration. The method further comprises identifying a pre-existing configuration, from a collection of pre-existing configurations that match the active ED configuration, the collection of pre-existing configurations having an associated collection of predefined parameter sets. The method further determines a resultant parameter set from the collection of predefined parameter sets based on the pre-existing configuration identified and returns the resultant parameter set in connection with the request, the resultant parameter set to be utilized by the ED for bi-directional communication with the IMD.

Optionally, the determining operation includes selecting multiple predefined parameter sets associated with the pre-existing configuration identified, wherein the determining operation including selecting the resultant parameter set based on a highest of at least one of a success rate or a data transfer rate. Optionally, the collection of the predefined parameter sets represents a collection for at least one of connection parameters or data transfer parameters.

Optionally, the connectivity parameters include at least one of connection retry timeout, inter-connect retry timeout, or supervision timeout, and the data transfer parameters include at least one of maximum interval, minimum interval, latency, supervision timeout. Optionally, the collection of predefined parameter sets include at least first and second predefined parameter sets for at least first and second battery conditions of the IMD, respectively, the request including a battery condition indication, the determining operation determining one of the first and second predefined parameter sets based on the battery condition indication.

In accordance with an embodiment herein, a computer implemented method is provided for managing bi-directional communication between an external device and an implantable medical device. The method comprises performing a connection operation and a data transfer operation between the ED and the IMD; determining, at the ED, a connection performance measure in connection with the connection operation. The method determines, at the ED, a transfer performance measure in connection with the data transfer operation; and transferring the connection and transfer performance measures from the ED to at least one of a local base station and a communications management resource.

Optionally, the connection and data transfer operations are performed in accordance with a self-calibration test. The connection operation may include detecting, at the ED, an advertisement transmitted from the IMD during a connection window. The connection transfer performance measure may represent an indication of a connection success rate during the connection window. Optionally, the data transfer operation includes detecting, at the ED, an amount of data transferred from the IMD during a data transfer interval, the connection performance measure representing an indication of a data transfer rate. The performing and determining operations may be repeated multiple times to obtain cumulative connection and transfer performance measures based on multiple connection operations and multiple data transfer operations.

In accordance with an embodiment herein, a system is provided for managing bi-directional communication between an external device and an implantable medical device. The system includes memory to store a collection of pre-existing configurations having an associated collection of predefined parameter sets, the memory to store program instructions. The system includes one or more processors that, when executing the program instructions, are configured to: receive an active ED configuration and a request for communications parameters to be used with the active ED configuration; and identify a pre-existing configuration, from the collection of pre-existing configurations, that matches the active ED configuration. The processors determine a resultant parameter set from the collection of predefined parameter sets based on the pre-existing configuration identified; and return the resultant parameter set in connection with the request, the resultant parameter set to be utilized by the ED for bi-directional communication with the IMD.

Optionally, the pre-existing configuration may be associated with first and second predefined parameter sets, the first and second resultant parameter sets having first and second performance measures, respectively, the determine operation including to select the first or second predefined parameter set based on which of the first and second performance measures is higher. The first and second performance measures may correspond to at least one of a connection success rate or a data transfer rate. Optionally, the active ED configuration includes at least two of geographic region, ED manufacturer, ED model, operating system version, RF chipset, RF stack/driver version, WiFi on/off state, and/or external power source connected to the ED. The determine operation may include searching a table stored in the memory, the table including the collection of pre-existing configurations for a plurality of ED, the table including the collection of predefined parameter sets and associated performance measures.

In accordance with an embodiment herein, a computer program product is provided comprising a non-signal computer readable storage medium comprising computer executable code to perform a connection operation and a data transfer operation between an external device (ED) and an implantable medical device (IMD). The program product determines, at the ED, a connection performance measure in connection with the connection operation; determining, at the ED, a transfer performance measure in connection with the data transfer operation; and transfers the connection and transfer performance measures from the ED to at least one of a local base station and a communications management resource.

Optionally, the connection and data transfer operations are performed in accordance with a self-calibration test. The connection operation may include detecting, at the ED, an advertisement transmitted from the IMD during a connection window. The connection performance measure may represent an indication of a connection success rate during the connection window. The data transfer operation may include detecting, at the ED, an amount of data transferred from the IMD during a data transfer interval, the connection performance measure representing an indication of a data transfer rate.

DETAILED DESCRIPTION

Figure 1:
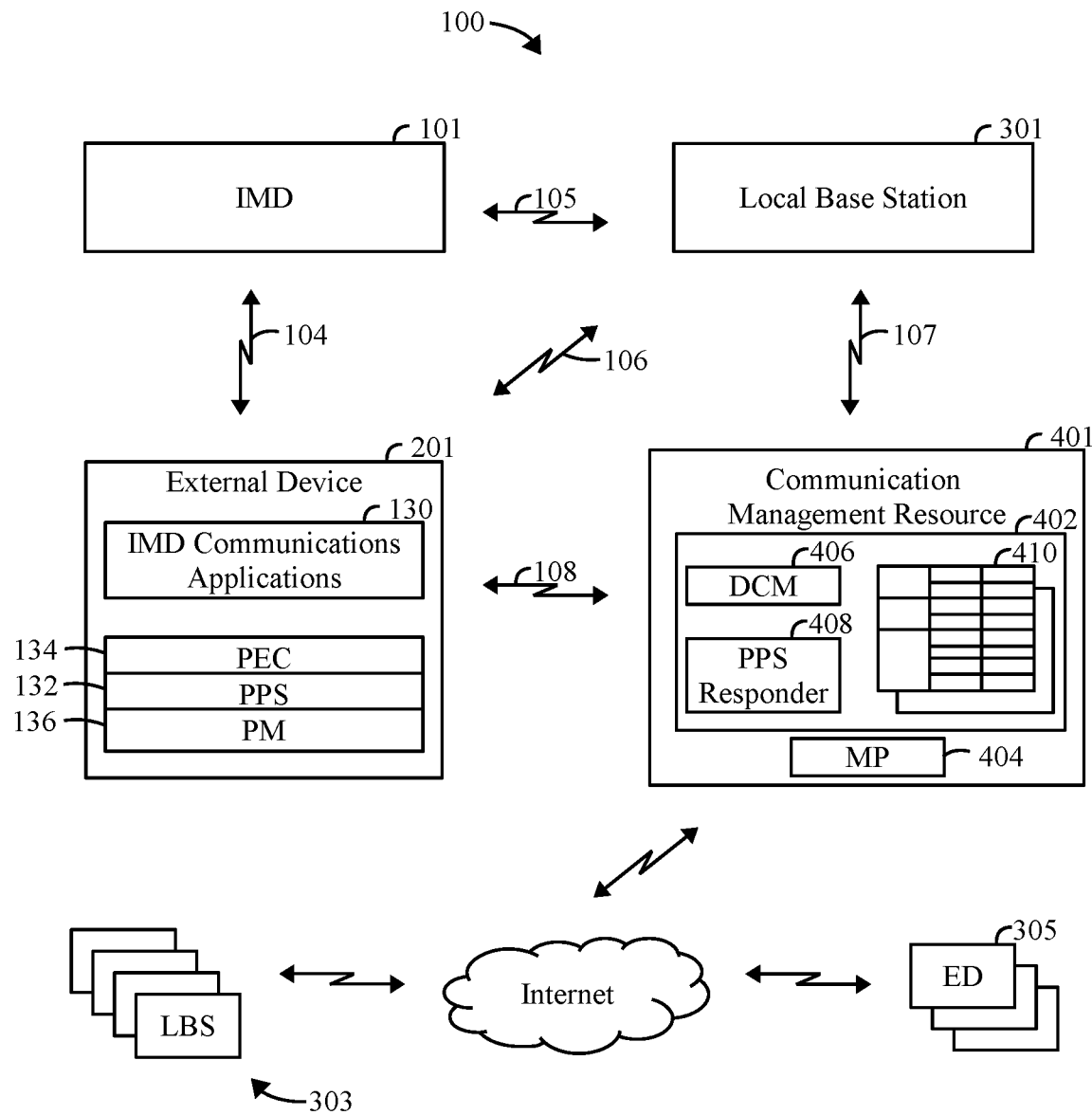
FIG. 1 illustrates simplified block diagram of a system for initiating a bi-directional communication link, according to an embodiment of the present disclosure.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

In accordance with embodiments herein, methods and systems are provided to determine desired (e.g., optimal) values for parameters used by an external device (ED) and implantable medical device in connection with establishing a communications connection and data transfer there between. In accordance with at least some embodiments, the parameter values may be identified through machine learning methodologies implemented on one or more communications management resources (e.g., cloud-based servers). Over time, the communications management resources collect performance measures concerning one or more characteristics of interest in connection with communications sessions for a large pool of EDs and IMDs. Based on the information collected over time, the communications management resources identify predetermined parameter sets that exhibit a preferred performance in connection with certain ED pre-existing configurations.

The communications management resources are then able to provide a predetermined parameter set (PPS) to be assigned in connection with an individual pre-existing configuration (PEC), with the PPS downloaded from a remote resource based on performance measures to afford a desired (e.g., optimal) connectivity and data transfer throughput. Embodiments herein also include a self-calibration process to identify communications parameters to be identified when no or few PEC and performance measures are available.

In accordance with embodiments herein, the methods and systems find preferred (e.g., optimal) BLE parameters for BLE communication between an ED (e.g., a given mobile device) and an IMD. A large variety of mobile devices may be utilized as an ED, such that each manufacturer and model of mobile device may use different BLE hardware and software drivers. The various hardware and software components will exhibit a large variation in performance. Embodiments herein account for the fact that parameters used for one mobile device configuration will not provide the same effectiveness of BLE communication for another mobile device configuration. Embodiments herein account for a diversity in commercial mobile devices, and adapt BLE communication parameters to achieve a desired performance measure, such as related to connection rate and data throughput.

Accordingly, embodiments herein afford better adaptability and expansion opportunity for future mobile devices. For example, desired combinations of PECs and PPSs may be determined through a collaborative sharing of information between external devices and the communications management resources. The communications management resources may be implemented through a cloud-based environment provides accuracy and field tested parameter values based on feedback from mobile devices. A closed loop feedback system is provided that is able i) to continuously improve accuracy, ii) to adapt to manufacturing changes for mobile device, and iii) to adapt to new mobile device models as introduced. The methods and systems avoid a need to make IMD related software updates for different or newer mobile devices and hence reduce a number of regulatory submissions. The methods and systems provide parameter values based on what has been found to work most in the field.

Terms

The term "communications parameter" refers to one or more parameters related to a wireless protocol of interest. Non-limiting examples of wireless protocols include Bluetooth Low Energy (BLE), Bluetooth, ZigBee, or the like. For example, the BLE protocol is defined within "Bluetooth Specification Version 4.1, published Dec. 3, 2013 (incorporated herein by reference). The BLE protocol is a master-slave protocol operating within a frequency range of 2400-2483.5 MHz (including guard bands). The BLE protocol uses 20 RF channels using a 2 MHz bandwidth. The 20 RF channels are allocated into two channel types, a data channel (having 37 channels) and an advertising channel (having 3 channels). The data channel is used by devices on a BLE network for communication between connected devices. The advertising channel is used by devices on the BLE network to discover new devices, initiate a connection, and broadcast data. Each RF channel (data and advertising channel) is allocated a unique channel index, such that, if two devices wish to communicate, the transceivers of each device must be tuned to the same RF channel at the same time. Optionally, additional or alternative communications protocols may be utilized.

The term "performance measure" refers to one or more characteristic of interest that relate to a connectivity operation and/or a data transfer operation. Nonlimiting examples of a transfer performance measure include a data transfer rate, a number of errors exhibited during a data transfer operation and the like. Nonlimiting examples of a connectivity performance measure include a count of the number of connections that occurred during different connection windows, a percentage of successful connections during different connection windows and the like.

The term "configuration element" refers to hardware and/or software of an ED that influence or affect a performance measure of a connectivity operation and/or a data transfer operation. Non-limiting examples of configuration elements include, geographic region, ED manufacturer, ED model, operating system version, RF chipset, RF stack/driver version, WiFi on/off state, and/or external power source connected.

The terms "pre-existing configuration" and "PEC" refer to an individual combination of configuration elements that is implemented on an external device. By way of example, an "active ED configuration" refers to a pre-existing configuration that is in use on a particular ED in accordance with embodiments herein.

The terms "predefined parameter sets" and "PPS" refer to a combination of values assigned to parameters related to hardware and/or software of the ED and/or IMD that is utilized in connection with establishing and maintaining connectivity and data transfer during a communications session between the ED and IMD.

The terms "PPS1, PPS2, PPSn" refer to Pre-defined Parameter Set 1, Pre-defined Parameter Set 2, . . . , Pre-defined Parameter Set N, where N is a positive integer number.

The term "N" refers to a number of iterations which is a positive integer number greater than 0.

The terms "T1, T2" refer to connection windows (e.g., in seconds) following initiation of an attempt to connect.

The terms "CR1, CR2" refer to first and second connection rates (e.g., as a percentage %) for T1 and T2.

The terms "CRT1, CRT2" refer to first and second connection rates threshold (e.g., as a percentage %).

The term "TID" refers to test iteration duration (e.g., in seconds). For example, the TID may correspond to a period of time that an ED attempts to make a connection following a direction to connect. Additionally or alternatively, a TID may correspond to a period of time during which a data transfer operation occurs.

The term "DTR" refers to a data transfer rate (e.g., as a percentage %).

The term "DTRT" refers to a data transfer rate threshold (e.g., as a percentage %).

A non-limiting list of BLE connection parameters includes: Connection Retry Timeout, Inter Connect Retry Timeout, and Supervision Timeout.

A non-limiting list of BLE data transfer parameters includes: Normal Min Interval, Normal Max Interval, Normal Latency, Normal Supervision Timeout, Low Battery Min Interval, Low Battery Max Interval, Low Battery Latency, and Low Battery Supervision Timeout.

System Overview

FIG. 1 illustrates a simplified block diagram of a system 100 to manage a bi-directional communication link 104 between an external device (ED) 201 and an implantable medical device (IMD) 101. The system 100 attempts to obtain a desired performance of communication. For example, in some embodiments, the system 100 seeks to optimize communication or maintain communications within a desired performance level. The system 100 also includes a local base station (LBS) 301 configured to communicate with one or both of the IMD 101 and the external device 201 over bidirectional communications links 105 and 106. The local base station 301 is also configured to communicate with a communications management (CM) resource 401 over a bidirectional communications link 107. As one example, the communications link 107 may pass through various intermediate networks, wireless or wired communications equipment, the Internet and the like. Additionally or alternatively, the external device 201 may be configured to communicate directly with the CM resource 401 through communications link 108. As one example, the communications link 108 may pass through various intermediate networks, wireless or wired communications equipment, the Internet and the like.

FIG. 1 also illustrates a plurality of LBS 303 and ED 305 that may communicate through the Internet with the CM resource 401. As explained herein, the CM resource 401 collects information from multiple EDs 305 and utilizes machine learning techniques to identify preferred parameter sets to be utilized in connection with various ED pre-existing configurations.

The external device 201 may be a table computer, smart phone, laptop, or other stationary or portable device having bi-directional communication capability. The CM resource 401 may represent a single or distributed server or server network, a healthcare network computing system, a workstation and the like. The bi-directional communication links 104-108 may use any standard wireless protocol such as Bluetooth Low Energy, Bluetooth, Wireless USB, Medical Implant Communication Service, ZigBee, and/or the like that define a means for transmitting and receiving information (e.g., data, commands, instructions) between devices. The external device 201 and/or local base station 301 may convey various types of information to the IMD 101 (e.g., operational information, programmable parameters, etc.). The external device 201 and/or local base station 301 may receive various types of data from the IMD 101. In various embodiments, the local base station 301 may be a portable and/or handheld device allowing the user to position and/or reposition the local base station 301 within a room (e.g., on a night stand near a bed, etc) and/or in varying proximities to the patient. Additionally or alternatively, the local base station 301 may be mounted and/or integrated to another structure. For example, the local base station 301 may be mounted to a bed of the patient 106, a patient monitoring system, and/or the like.

While the IMD 101 is implanted within the patient (e.g., proximate to a heart, proximate to the spinal cord or elsewhere), additionally or alternatively, the IMD 101 may have components that are external to the patient. For example, the IMD 101 may include a neuro external pulse generator (EPG). The IMD 101 may be one of various types of implantable devices, such as, for example, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like.

Example block diagrams of an IMD 101, and external device 201 and are described below in more detail in connection with FIGS. 5-6.

As explained herein, when first initiated, a new external device 101 loads an IMD communications application 130. The external device 101 includes a pre-existing configuration 134 of hardware and software elements utilized in connection with communications. Optionally, the IMD communications application 130 may review the internal configuration of the external device 101 to identify the pre-existing configuration 134 (e.g., identify the operating system, manufacturer, model, communications chipset, communications driver versions, etc.). The IMD communications application 130 steps through initial connectivity and transfer parameters until determining a desired combination of connectivity and transfer parameters, to be designated as a first predetermined parameter set. As one example, the IMD communications application 130 may be initially set up with standard connectivity and transfer parameter values. The IMD communications application 130 may perform a self-calibration test related to a connectivity operation and a data transfer operation (e.g., FIGS. 2B and 2C). The IMD communications application 130 may iteratively increment or decrement one or more parameter values until achieving a desired performance. The performance is characterized by a performance measure, such as a desired connection success rate during the first or second connection windows and/or a desired data transfer rate. When desired performance measures 136 are achieved, the corresponding connectivity and transfer parameter values are saved as a predetermined parameter set 132. The predetermined parameter set 132, pre-existing configuration 134, and performance measures 136 are sent to the CM resource 401 data mining purposes.

The CM resource 401 continuously collects PPS 132, PEC 134 and related performance measures 136 for multiple external devices that have different pre-existing configurations. The CM recourse 401 includes memory 402 and one or processors 404 that implement a data collection module 406 and a PPS responder 408 that perform the operations of the CM resource 401 as described herein. The memory 402 includes a table 410 that is built and maintained by the data collection module 406 to collect statistics in connection with connection rate, overall connectivity, data transfer rate, data transfer reliability and the like. The table 410 includes various fields to track configuration elements, parameters and performance measures as described herein.

In accordance with one embodiment, the table 410 combines connectivity and data transfer parameters. Optionally, the table 410 may include one table for BLE connectivity parameters and one table for BLE data transfer parameters. By way of example, the following fields represent fields that may be maintained within the table 410, namely Region, Manufacturer, Model, OS version, BLE Chipset, BLE Stack/Driver version, PPS1 and corresponding success rate, PPS2 and corresponding success rate, PPSn and corresponding success rate. Based on the data collected for various mobile devices, the success rate for PPS1, PPS2, etc. will change. When the IMD communication application requests BLE parameters, the pre-defined parameter set with highest success rate at that point in time may be provided as a response. This allows the data in the table on the CM resource (e.g., server) side to adapt and learn continuously based on feedback from field mobile devices.

Thereafter, when a new/second external device utilizes the same pre-existing configuration as a prior/first ED, the CM resource 401 is able to send to the second ED the PPS (from the first ED) as a starting point. The first and second ED send statistics on success rates using the PPS. The CM resource 401 uses the success rates as a weighting factor for the corresponding PPS in accordance with determining suitable (e.g., best) values for a given device configuration. If there is any need to adjust original PPS values based on feedback from other ED, the CM resource 401 will adjust the PPS values and provide new PPS values when requested by EDs.

The data collection module 406 receives information from numerous local base stations (which serve as relays for information from external devices and IMD's). Additionally or alternatively, the data collection module 406 may receive information directly from the external devices 201 without the use of an intervening local base station. The data collection module 406 updates the table 410, such as by adding and removing pre-existing configurations. The data collection module 406 also adds, modifies and removes predetermined parameter sets and corresponding performance measures in connection with pre-existing configurations. The PPS responder 408 receives requests from LBSs 301, 303 and/or EDs 101, 305, matches incoming active ED configurations with the collection of PECs in the table 410. The PPS responder 408 identifies one or more PPS to be returned to an ED 201 based on the various criteria discussed herein. The data collection module 406 and the PPS responder 408 perform a machine learning process, as described herein, to determine desired (e.g., optimal) values for one or more parameters associated with various EDs.

The PPS responder 408 may be implemented by one or more processors 404 that, when executing the program instructions, are configured to receive an active ED configuration and a request for communications parameters to be used with the active ED configuration. The PPS responder 408 identifies a pre-existing configuration, from the collection of pre-existing configurations that matches the active ED configuration. The PPS responder 408 determines a resultant parameter set from the collection of predefined parameter sets based on the pre-existing configuration identified. The PPS responder 408 returns the resultant parameter set in connection with the request, the resultant parameter set to be utilized by the ED 201 for bi-directional communication with the IMD.

For example, the pre-existing configuration may be associated with first and second predefined parameter sets. The first and second resultant parameter sets may have first and second performance measures, respectively. The PPS responder 408 selects the first or second predefined parameter set based on which of the first and second performance measures is higher.

Communication Management Processes

FIGS. 2A-2D illustrate flowcharts for managing the bi-directional communication link between the external device (e.g., 201) and the implantable medical device (e.g., 101). The methods of FIGS. 2A-2D may be implemented as a software algorithm, package, or system that directs one or more hardware circuits or circuitry to perform the actions described herein. FIGS. 2A-2D, illustrate methods that seek to optimize communication or maintain communications within a desired performance level. For example, the operations of the methods may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

For example, the ED 201 may initiate an attempt in response to an instruction from a patient or physician. For example, a patient may instruct the ED 201 to initiate a connection with the IMD 101 when the patient feels particular certain behavior. Optionally, the ED 201 may initiate an attempt in response to a "command to connect" received from the CM resource 401 and/or the LBS 301. In the example of FIGS. 2A-2D the "active" ED represents ED 201 that is currently performing all or some of the operations of FIGS. 2A-2D.

Figure 2A:
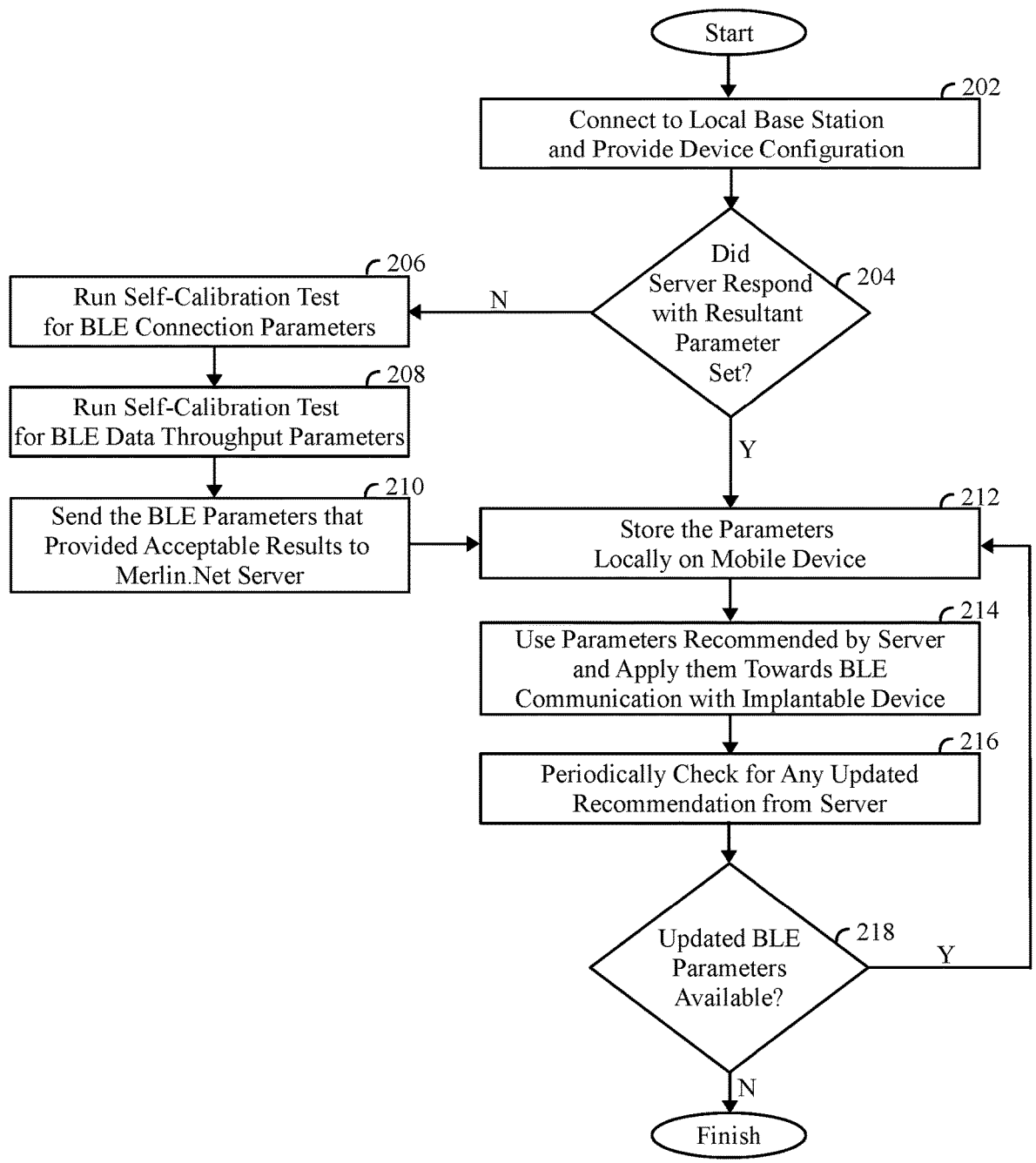
FIG. 2A illustrates a flowchart for managing the bi-directional communication link between the external device and the implantable medical device in accordance with embodiments herein.

With reference to FIG. 2A, at 202, one or more processors of the ED 201 connect to the local base station and provide ED 201 information including the active ED 201 configuration of the ED 201. The ED 201 also conveys a request for communications parameters to be used by the ED 201. Optionally, the ED 201 may provide a battery condition indicator. For example, the ED 201 may provide one of first and second battery condition indicators, as well as more than two battery condition indicators. The LBS 301 retransmits the active ED 201 configuration, request, battery condition indicator and other ED 201 information to the CM resource 401. The CM resource 401 processes the request, as described herein, and returns one or more resultant parameter sets. Optionally, the LBS 301 may not pass on the active ED 201 configuration, request, battery condition indicator and other ED 201 information to a CM resource 401. Instead, the LBS 301 may process the active ED 201 configuration, request, battery condition indicator and other ED 201 information as described herein (e.g., FIG. 4) and return one or more resultant parameter sets.

With respect to FIG. 1, the ED 201 represents an active ED 201 that includes an active ED 201 configuration. The active ED 201 configuration includes at least two of geographic region, ED 201 manufacturer, ED 201 model, operating system version, RF chipset, RF stack/driver version, WiFi on/off state, and/or external power source connected to the ED 201. The PPS responder 408 (FIG. 1) of the CM resource 401 searches the table 410 stored in the memory 402. The table 410 includes the collection of pre-existing configurations, the collection of predefined parameter sets and associated performance measures.

Optionally, the ED 201 may connect to the CM resource 401 without utilizing a LBS 301. For example, the ED 201 may utilize a cellular or other wireless network to communicate directly with the CM resource 401 over the Internet, a local area network or a wide area network that does not utilize a LBS 301.

At 204, the one or more processors of the ED 201 determine whether one or more resultant parameter sets is returned in response to the request. For example, multiple resultant parameter sets may be returned when the CM resource 401 determines that more than one resultant parameter set represents a potential candidate. For example, two or more resultant parameter sets may have similar performance measures. When similar performance measures have been recorded in connection with the same PEC 134, the CM resource 401 may pass each of the corresponding PPS two a requesting/active ED 201. When no resultant parameter set is returned, flow moves to 206. When one or more resultant parameter sets is returned, flow moves to 212.

Optionally, the CM resource 401 may return, as part of the resultant parameter set, a range or a starting value for one or more of the parameters. The CM resource 401 may also return a step size, by which one or more of the parameters may be increased or decreased as the ED 201 and IMD 101 step through a range of potential values for the one or more parameters in search of a performance measure that satisfies select criteria.

Additionally or alternatively, the CM resource may return one or more resultant parameter sets to be used when the ED 201 experiences different operating conditions as part of the PEC 134. For example, when the Wi-Fi is active on the ED 201, the ED 201 may use one resultant parameter set. When the Wi-Fi is inactive on the ED 201, the ED 201 may utilize another resultant parameter set. As another example, when the ED 201 is connected to a power source, one resultant parameter set may be utilized. When the ED 201 is disconnected from a power source, another resultant parameter set may be utilized. Additionally or alternatively, the CM resource 401 may return one or more ranges or starting values (with or without steps) for one or more parameters to be utilized when the ED 201 experiences different operating conditions as part of the PEC 134. For example, when the ED 201 switches between a Wi-Fi active and Wi-Fi inactive state, the ED 201 may iteratively adjust one or more parameters over a range of values in search of preferred performance measures. Similarly, when the ED 201 is disconnected from or connected to a power source, the ED 201 may initiate an iterative adjustment of one or more parameters in search of a preferred performance measure.

At 206, the one or more processors of the ED 201 perform a self-calibration test in connection with connectivity parameters. Example operations of the connectivity self-calibration test are described herein in more detail. The self-calibration test 206 (described in more detail with respect to FIG. 2B) may do N number of iterations as defined in software or until an acceptable parameter set is found (e.g., a parameter set yields desired performance measures), whichever is earlier. During each iteration, the process uses one Pre-defined Parameter Set (e.g., PPS1, PPS2) and tries to establish connections with the implantable medical device for a period of time specified by TID. After completion of the TID period of time, the ED 201 evaluates the connection success rate for time/connection windows T1 and T2. Successful connection rates during T1 and T2 are indicated by CR1 and CR2 (e.g., as percentages %). As one example, if CR1 and CR2 are above an acceptable threshold value CRT1 and CRT2, respectively, the Pre-defined Parameter Set is classified as acceptable. For example, the comparison to the threshold values CRT1 and CRT2 may be performed at the ED 201. When the comparison is made at the ED 201, and the threshold values CRT1 and CRT2 are satisfied, the Pre-defined Parameter Set is considered acceptable, and the ED 201 transmits the PPS, PEC and performance measures to the CM resource 401 as feedback along with other relevant statistics.

Additionally or alternatively, the LBS 301 and/or CM resource 401 may compare the CR1 and CR2 to the threshold values CRT1 and CRT2.

At 208, the one or more processors of the ED 201 perform a self-calibration test in connection with data transfer/throughput parameters. Example operations of the self-calibration test for data transfer are described herein in more detail. The self-calibration test 208 (described in more detail with respect to FIG. 2C) may do N number of iterations as defined in software or until an acceptable parameter set is found (e.g., a parameter set yields desired performance measures), whichever is earlier. During each iteration, the process uses one Pre-defined Parameter Set (e.g., PPS1, PPS2) and the ED attempts to read a fixed number of bytes from the IMD 101 for a period of time specified by TID. During the data transfer operation, the IMD 101 communications application 130 (FIG. 1) evaluates the data transfer rate DTR. A successful data transfer rate is indicated when the data transfer rate crosses the pre-defined data transfer rate threshold (DTRT). The ED 201 determines whether the data transfer rate exceeds the threshold. If DTR is acceptable, the ED 201 determines that the Pre-defined Parameter Set is considered acceptable. When the ED 201 classifieds the Pre-defined Parameter Set to be acceptable, the ED 201 transmits the PPS, PEC and performance measures to the CM resource 401 as feedback along with other relevant statistics.

Additionally or alternatively, the LBS 301 and/or CM resource 401 may determine whether the data transfer rate DTR exceeds the threshold DTRT.

At 210, the one or more processors of the ED 201 transmit, to the LBS 301 and/or CM resource 401, one or more connectivity parameter sets and/or data transfer parameter sets, along with the corresponding performance measures. For example, the ED 201 may transmit a PPS that includes a connectivity parameter set and/or data transfer parameter set, where the PPS exhibits a predetermined level of performance measures (e.g., the highest rate of success for connection, the high data transfer rate).

At 212, the one or more processors of the ED 201 store the one or more resultant parameter sets locally in memory of the ED 201. The one or more resultant parameter sets may be determined at 206-210 by the ED 201, or alternatively provided by the CM resource 401 and/or LBS 301.

At 214, the one or more processors of the ED 201 use the resultant parameter set in connection with communications with the IMD 101. When more than one resultant parameter set is returned from the CM resource 401 or determined at 206-210, the ED 201 may cycle through the available resultant parameter sets and determine a one of the resultant parameter sets that affords the best performance measures for the particular ED 201. At 216, the one or more processors of the ED 201 periodically check for any updated PPS. At 218, when an updated PPS is available, flow returns to 212. Otherwise, the process ends.

Figure 2B:
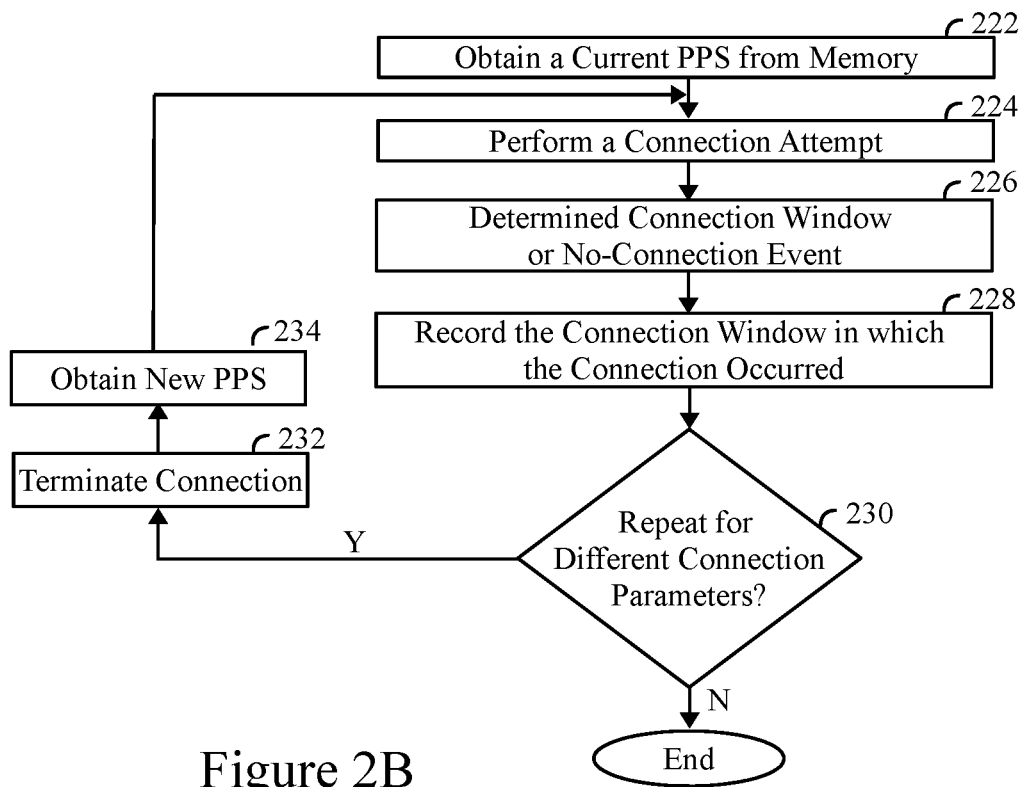
FIG. 2B illustrates a process for performing a self-calibration test for establishing connectivity in accordance with embodiments herein.

FIG. 2B illustrates a process for performing a self-calibration test for establishing connectivity in accordance with embodiments herein. The self-calibration test for connectivity may be initiated for the reasons described above in connection with FIG. 2A. Additionally or alternatively, the connectivity self-calibration test may be performed periodically on a predetermined interval (e.g., weekly, monthly, yearly). Additionally or alternatively, the connectivity self-calibration test may be run post-implant. As explained hereafter, the connectivity self-calibration test is performed based upon a known advertisement rate utilized by the IMD 101 throughout operation. Additionally or alternatively, the advertisement rate utilized by the IMD 101 may be temporarily modified, such as to increase temporarily the advertising frequency (e.g., increase from one advertisement per four minutes to one advertisement every minute). It may be desirable to increase the advertisement rate of the IMD 101 for a temporary period of time shortly after implant. Additionally or alternatively, the connectivity self-calibration test may be performed each time a configuration element of the ED 201 is updated, such as when the ED 201 updates its operating system, drivers, firmware and the like. Optionally, the self-calibration test may be performed when security patches are applied to the ED 201.

At 222, the one or more processors of the ED 201 obtain a current PPS from memory. For example, one or more PPS may be stored in memory of the ED 201 at the time that the communications application is uploaded, when the ED 201 is registered with a medical network in connection with a particular IMD 101 and the like.

At 224, the one or more processors of the ED 201 perform a connection attempt with the current PPS. For example, the ED 201 may begin to listen for an advertisement from the IMD 101 over one or more predetermined channels as defined by a communications protocol and the PPS. In the event that a connection is not established immediately, the connection attempt may be maintained for a predetermined period of time. For example, the ED 201 may continue to listen for advertisements from the IMD 101 for a period of time corresponding to a select number of advertisement period (e.g., 2-5). The IMD 101 may be programmed to broadcast advertisements spaced apart by a predetermined period (e.g., one advertisement every 2-5 minutes). Various advertisement intervals may be utilized. Additionally or alternatively, a series of advertisements may be transmitted with the advertisements spaced apart by a first interval, followed by a longer interval before the series of advertisements are repeated. At 224, the advertisement period is used as a basis to define an amount of time, referred to as connection test iteration duration (TID), during which the ED 201 listens/searches for advertisements.

At 226, the one or more processors of the ED 201 determine the connection window during which the connection was successful. Alternatively, at 226, the processors may determine that no connection was established (corresponding to a "no connect event"). The connection TID may be divided into two or more connection windows starting at the time that the ED 201 initiates an attempt to communicate with the IMD 101. When the ED 201 initiates an attempt to connect, a connection timer may be started. When a connection is made, the connection timer is compared to the advertisement period to determine which of the connection windows, the connection occurred. For example, when the advertisement period is three minutes and the ED 201 takes two minutes to connect (following initiation of a connection attempt), the processor of the ED 201 would record that a successful connection was made during the first connection window. Alternatively, if the ED 201 took 5 minutes to connect, the processor of the ED 201 would record that a successful connection was made during the second connection window.

At 228, the one or more processors of the ED 201 record the connection window in which the connection occurred. At 230, the one or more processors determine whether to repeat the connection process in connection with different connectivity parameters. When different connectivity parameters are to be tested, flow moves to 232.

At 232, the current connection is terminated. At 234, a new PPS is obtained from memory. For example, the new PPS may be pre-stored. Alternatively, the new PPS may be created by decreasing/increasing one or more of the previous PPS by a predetermined step amount. Thereafter, flow returns to 224 and the operations at 224-228 are repeated. The operations between 224 and 234 are repeated a desired number of times until obtaining a desired amount of information concerning performance measures for connectivity parameters. For example, 1-10 different sets of PPS may be considered during the self-calibration test of FIG. 2B. When the operations of FIG. 2B are completed, the related performance measures or underlying connection information are passed to the LBS 301 and/or CM resource 401.

The performance measures represent an indication of a connection success rate during a corresponding connection window, where the success rate is relative to a total number of attempted connections. For example, when 10 connections are attempted, the performance measures may indicate an 80% connection success rate (e.g., eight out of ten) during the first connection window and a 20% connection success rate (e.g., two out of ten) during the second connection window. As another example, the connection success rate may indicate a number of successful connections achieved during a corresponding connection window relative to only the number of attempted connections that occurred during the window. For example, when 10 connections are attempted and eight of the connections occurred during the first connection window, only two connections would be attempted during the second connection window. Accordingly, the success rate during the second connection window may be 100%, when considered relative only to connections attempted during the second connection window.

The ED 201 may track the number of successful connections in each connection window in various manners. For example, the processor of the ED 201 may designate first and second counters for first and second connection windows, respectively. Each time a successful connection is made during the first connection window, the first counter is increments. Each time a successful connection is made during the second connection window, the second counter is incremented. The ED 201 may maintain a total attempt counter to track the total number of times that the ED 201 attempts to connect. The relation between the first and total attempt counters indicates a success rate during the first connection window, while the relation between the second and total attempt counters indicate a success rate during the second connection window. As explained herein, the success rates represent one type of performance measurement that is transmitted from the ED 201 to the CM resource 401 periodically or on demand.

When the success rates are transmitted to CM resource 401, the first, second and total attempt counters may be reset. Alternatively, the first, second and total attempt counters may continue to be incremented so long as an active ED 201 configuration is utilized by the ED 201. When the active ED 201 configuration is changed, the first, second and total attempt counters may be reset.

Figure 2C:
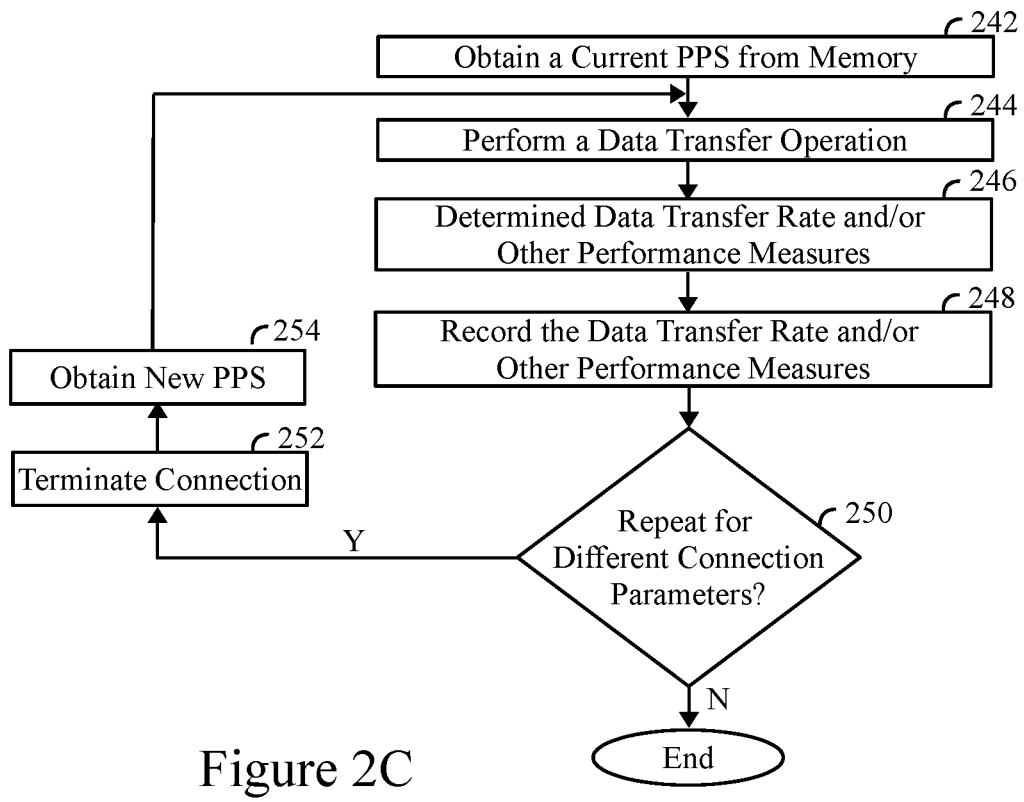
FIG. 2C illustrates a process for performing a self-calibration test for establishing performance measure for data transfer in accordance with embodiments herein.

FIG. 2C illustrates a process for performing a self-calibration test for establishing performance measure for data transfer in accordance with embodiments herein. The data transfer self-calibration test may be implemented in all or a portion of the foregoing situations described in connection with performing a connectivity self-calibration test. For example, any time a connectivity self-calibration test is performed, the data transfer self-calibration test may also be performed. Additionally or alternatively, either of the self-calibration tests may be performed independently.

While the operations of FIGS. 2B and 2C are described separately, it is understood that the processes therein may be performed in parallel or serial manners in either order. At 242, the one or more processors of the ED 201 obtain a current PPS from memory. At 244, the one or more processors of the ED 201 perform a data transfer operation. For example, the ED 201 may direct the IMD 101 to transfer a prerecorded string of data to the ED 201. The data to be transferred may be pre-recorded calibration related data (e.g., associated with a test mode). Additionally or alternatively, the data transfer self-calibration test may utilize data collected and stored by the IMD 101 in connection with normal operation (e.g., EGM data, episode related data, IMD 101 status data and the like). The performance measure of data transfer may be defined in various manners. For example, the ED 201 may record a total time needed to transfer a certain amount of data, and/or a total number of data packets or frames needed to transfer the data. Additionally or alternatively, the ED 201 may record the number of errors that occur during the data transfer and resulted in a need to retransmit portions of the data. Additional and alternative information may be recorded in connection with the performance measure of data transfer.

At 246 the one or more processors of the ED 201 determine the data transfer rate and/or other performance measures of data transfer. Alternatively, at 226, the processors may determine that no data transfer occurred (corresponding to a "no transfer event"). At 248, the one or more processors of the ED 201 record the data transfer rate and/or other performance measures of data transfer. At 250, the one or more processors determine whether to repeat the connection process in accordance with different data transfer parameters. When different data transfer parameters are to be tested, flow moves to 252. At 252, the current connection is terminated. At 254, a new PPS is obtained from memory. For example, the new PPS may be a pre-stored set of parameters. Alternatively, the new PPS may be determined by decreasing/increasing one or more of the previous PPS by a predetermined amount. Thereafter, flow returns to 244. The operations between 244 and 254 are repeated a desired number of times until obtaining a desired amount of information concerning performance measures for data transfer parameters. For example, 1-10 different sets of PPS may be considered during the self-calibration test of FIG. 2C. When the operations of FIG. 2C are completed, the related performance measures or underlying data transfer information are passed to the LBS 301 and/or CM resource 401.

In accordance with the operations of FIG. 2C, the data transfer self-calibration test detects, at the ED 201, the amount of data transferred from the IMD 101 during one or more predetermined data transfer intervals. The transfer performance measure recorded in connection there with represents an indication of the data transfer rate.

Figure 2D:
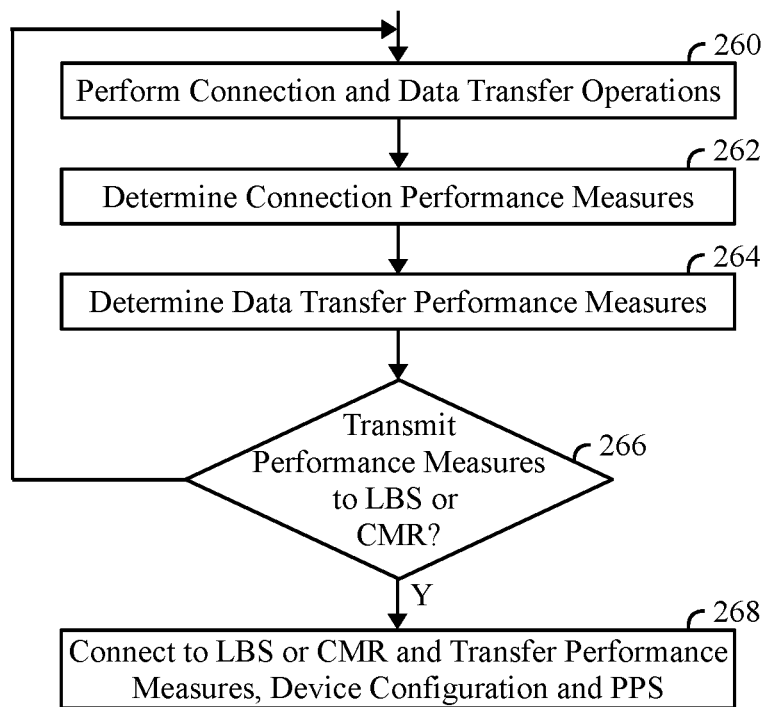
FIG. 2D illustrates a process carried out by an ED in connection with day-to-day communication between an ED and an IMD in accordance with an embodiment herein.

FIG. 2D illustrates a process carried out by an ED 201 in connection with day-to-day communication between an ED 201 and an IMD 101 in accordance with an embodiment herein. The operations of FIG. 2D may be performed after the ED has been assigned and implements a resultant parameter set in accordance with day-to-day operation. At 260, the one or more processors of the ED 201 use a current PPS, saved in memory of the ED 201, to perform a connection operation and a data transfer operation. At 262, the one or more processors of the ED 201 determine and save connectivity performance measures. As explained herein, the connection performance measures may represent a success rate for which successful connections were established in connection with one or more connection windows. At 264, the one or more processors of the ED 201 determine and save data transfer performance measures. As explained herein, the data transfer performance measures may indicate a data transfer rate, a number of errors occurring during a communications session and the like. At 262 and 264, the performance measures may be saved in connection with a single connection and data transfer operation. Additionally or alternatively, at 262 and 264, cumulative performance measures may be maintained in connection with multiple prior connection and data transfer operations. For example, the ED 201 may implement connection and data transfer operations with the IMD 101 over the course of a few weeks, months or years. Each time a connection and/or data transfer operation occurs, the ED 201 may update one or more existing cumulative performance measures. For example, the update may involve incrementing one or more counters (e.g., a count of the number of successful connections during each window). As another example, the update may combine a new data transfer rate (determined during a current data transfer operation) with a pre-existing cumulative data transfer rate (corresponding to one or more prior data transfer operations).

At 266, the one or more processors of the ED 201 may determine whether it is appropriate to transmit the performance measures to the local base station (LBS) 301 and/or CM resource (CMR) 401. For example, new performance measures may only be transmitted periodically (e.g., monthly, quarterly etc.). Additionally or alternatively, new performance measures may be transmitted based on performance measure thresholds. For example, when the data transfer rate falls below or exceeds thresholds, the data transfer rate and corresponding PPS may be transmitted to the LBS 301 and/or CM resource 401. As another example, the performance measures and corresponding PPS may be transmitted when a count of the number of connections that occurred during a particular connection window exceeds a threshold or percentage (e.g., when less than 75% or more than 95% of the connections occurred during the first connection window).

When the processors determined that performance measures should not be transmitted from the ED 201, flow returns to 260. Alternatively, when it is determined that performance measures are to be transmitted, flow moves to 268. At 268, the ED 201 establishes a connection with a LBS 301 and/or CM resource 401 and transfers the current PEC, PPS and related performance measures. Optionally, when performance measures are transferred from an ED 201, an LBS 301 or CM resource 401, at 268, the stored performance measures within the ED 201 may be reset or erased, such that subsequent performance measures are recorded only in accordance with new connection and data transfer operations. Alternatively, after 268, the pre-existing performance measures may be maintained and updated based on subsequent operations. Thereafter, the process of FIG. 2D ends.

Figure 3A:
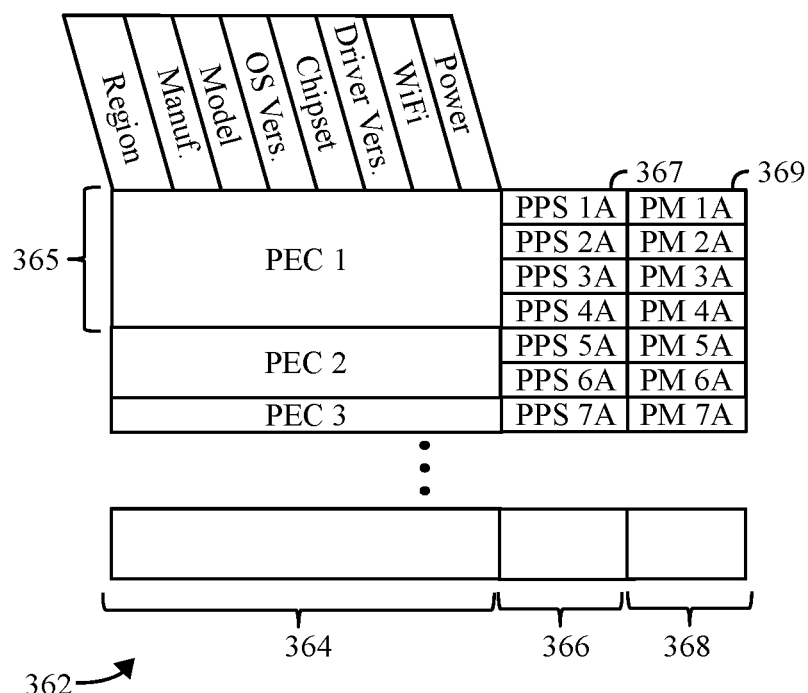
FIG. 3A illustrates a table utilized to track pre-existing configurations, connectivity parameter sets and performance measures in accordance with embodiments herein.

FIG. 3A illustrates a table utilized to track pre-existing configurations, connectivity parameter sets and performance measures in accordance with embodiments herein. The table 362 may be partially or entirely stored in memory at an LBS 301, CM resource 401, ED 201 or elsewhere. The table 362 includes a collection of pre-existing configurations (PEC) 364, an associated collection of predefined parameter sets (PPS) 366 (corresponding to connectivity parameters) and corresponding connectivity performance measures 368.

Figure 3B:
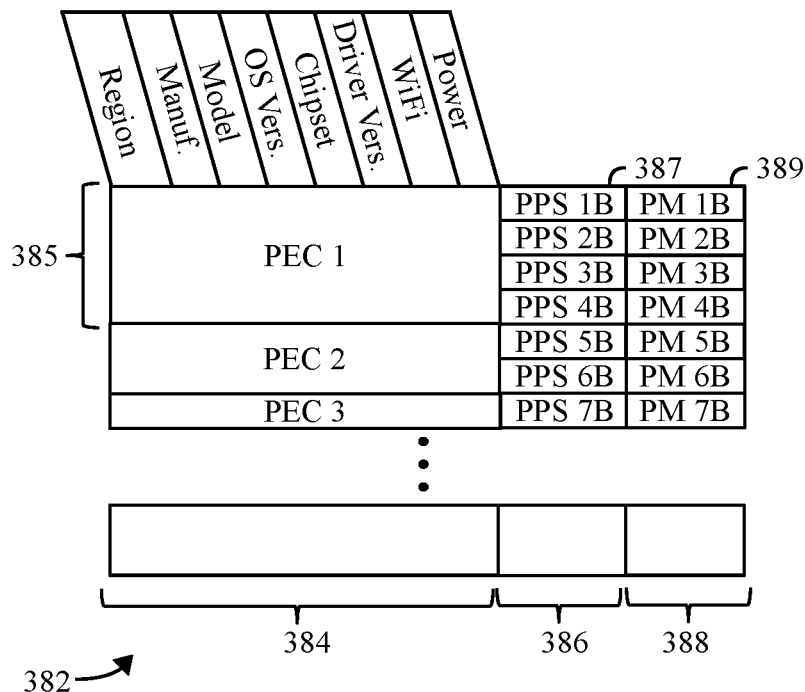
FIG. 3B illustrates a table utilized to track pre-existing configurations, connectivity parameter sets and performance measures in accordance with embodiments herein.

FIG. 3B illustrates a table utilized to track pre-existing configurations, connectivity parameter sets and performance measures in accordance with embodiments herein. The table 382 may be partially or entirely stored in memory at an LBS 301, CM resource 401, ED 201 or elsewhere. The table 382 includes the same collection of pre-existing configurations (PEC) 384 (corresponding to the PEC's 364). The table 382 also includes an associated collection of predefined parameter sets (PPS) 386 (corresponding to transfer parameters) and corresponding transfer performance measures 388.

The information stored in the tables 362, 382 may be organized and accessed from any manner of data sources, such as data bases, text files, data structures, libraries, relational files, flat files and the like. For ease of explanation, the data source typically is described herein in the form of a table, but it will be understood other data-management techniques and processes can be used. The table may be updated and manipulated until over the course of the data collection process.

As one example, the collection of PEC 364, 384 may be arranged as records 365, 385, each of which corresponds to one combination of configuration elements. For example, a row in the tables 362, 382 may represent unique PEC records 365, 385. Different combinations of configuration elements define different pre-existing configurations. An individual PEC record 365 (and/or 385) includes and is defined by at least two configuration elements. For example, geographic region may be relevant as ED 201 offered in certain geographic regions may include different hardware/software (e.g., based on local regulations) even though the ED 201 in two different geographic regions have the same manufacturer and model number and operating system. As another example, an on/off state of the WiFi may be relevant as the ED 201 may use the same antenna for WiFi and Bluetooth communications. When the WiFi is active, WiFi communications may create interference for Bluetooth based communications that are utilized in connection with embodiments herein. As another example, a connection to an external power source may be relevant as certain ED 201 may increase the transmit/receive power for wireless communications when an external power supply is connected, which in turn increases the probability of discovering a BLE peripheral device. Optionally, the ED 201 may decrease the transmit/receive power for wireless communications when an external power supply is not connected to conserve power.

With respect to FIG. 3A, the PEC records 365 are associated with one or more connectivity PPS 367 and a corresponding one or more connectivity performance measure 369. Non-limiting examples of connectivity parameters include at least one of connection retry timeout, interconnect retry timeout, or supervision timeout. For example, in FIG. 3A, the PEC1 is associated with four PPS1A-PPS4A, while PEC2 is associated with two PPS5A-PPS6A and PEC3 is associated with one PPS7A. The PPS1A-PPS7A have corresponding connection performance measures (e.g., BLE connection performance measure). For example, the PPS1A has a connection performance measure PM1A, while the PPS2A has a connection performance measure PM2A. The PPS3A-PPS7A has connection performance measures PM3A-PM7A, respectively (e.g., BLE connection performance measure).

With respect to FIG. 3B, the PEC records 385 are associated with one or more transfer PPS 387 and a corresponding one or more connectivity performance measure 389. Non-limiting examples of data transfer parameters include at least one of maximum interval, minimum interval, latency, supervision timeout. As in FIG. 3A, in FIG. 3B, the PEC1 is associated with four PPS1B-PPS4B, while PEC2 is associated with two PPS5B-PPS6B and PEC3 is associated with one PPS7B. The PPS1B-PPS7B have corresponding transfer performance measures. For example, the PPS1B has a data transfer performance measure PM1B. The PPS2B has a data transfer performance measure PM2B, while PPS3B-PPS7B has data transfer performance measures PM3B-PM7B, respectively.

Optionally, the information in FIGS. 3A-3B may be organized in different manners. For example, each record may have a single PEC, single PPS and performance measure, with duplicate records having the same PEC, the same or different PPC and the same or different performance measures. Alternatively, the information may be organized in other manners.

Additionally or alternatively, the tables 362, 382 may organize the PEC, PPS and performance measures in connection with different battery conditions. For example, different battery conditions may be defined for low and normal battery conditions. For example, a charge storage threshold may be defined, and when a battery charge condition drops below the charge storage threshold, the battery condition changes from a first/normal condition to a second/low condition. When different battery conditions are used, separate PPS may be maintained for each battery condition. For example, a first set of records may be maintained for first predefined parameter sets associated with the first/normal battery condition of the IMD 101, while a second set of records may be maintained for second predefined parameter sets associated with the second/low battery condition of the IMD 101. Further, additional or alternative battery conditions may be defined. Additionally or alternatively, the records may be maintained based on characteristics other than or in addition to battery condition, where such characteristics may have an effect on connection and/or data transfer performance. It is recognized that more than two battery conditions may exist (e.g., first, second, third, fourth and more).

Figure 4:
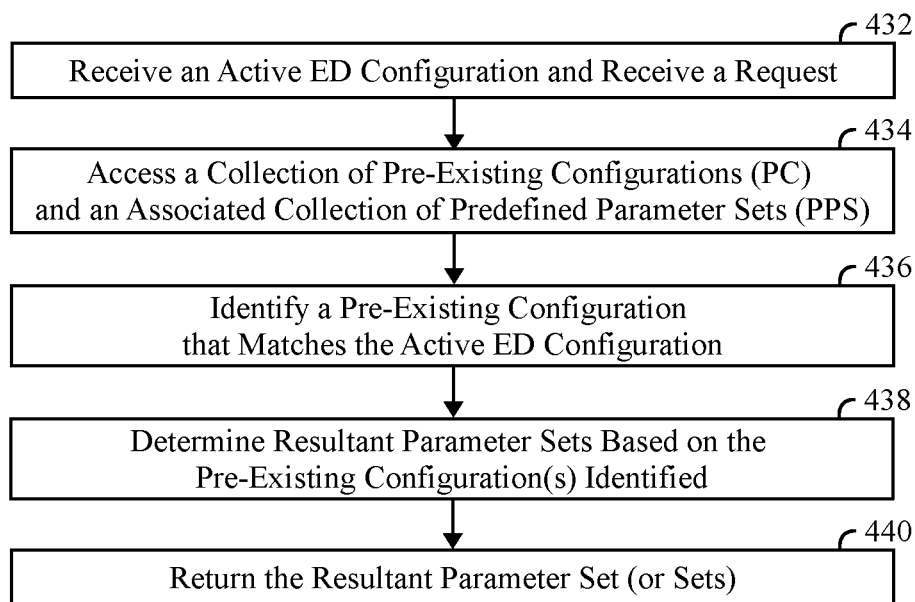
FIG. 4 illustrates a process for tracking ED configurations and performance measures for PPS, and for providing updates to PPS, in accordance with embodiments herein.

FIG. 4 illustrates a process for tracking ED 201 configurations and performance measures for PPS, and for providing updates to PPS, in accordance with embodiments herein. The process of FIG. 4 may be implemented by the CM resource 401, the LBS 301, the ED 201 and/or any combination thereof. Further, while the process of FIG. 4 is discussed in connection with one ED 201 and one IMD 101, it is understood that the process is carried out in connection multiple IMD 101 and multiple ED 201.

At 432, one or more processors of the CM resource 401 receive an active ED 201 configuration and receive a request for communications parameters to be used with the active ED 201 configuration. The request may originate at the ED 201 that transmits the request to the CM resource 401, such as through a wireless network (e.g., a cellular network, a wireless network, etc.). Additionally or alternatively, the request may be passed from the ED 201 to the local base station and the local base station then re-transmits the request to the CM resource 401. Additionally or alternatively, the request may originate at a local base station, such as periodically, or in response to a determination by the local base station that the configuration of the ED 201 has changed.

Optionally, the request may include a battery condition indication representing a condition of the battery (e.g., charge storage normal, charge storage low, etc.).

At 434, the one or more processors access a collection of pre-existing configurations, an associated collection of predefined parameter sets and corresponding performance measures in memory. For example, the processors may access a table stored in memory. The PECs, PPS and performance measures may be stored together or separately in a common memory or in separate memories. The PECs, PPS and performance measures may be maintained at a common CM resource 401 and/or local base station. Additionally or alternatively, all or a portion of the PECs, PPS and performance measures may be maintained, in duplicate, at multiple CM resources 401 and/or multiple local base stations 301. All or a portion of the PECs, PPS and performance measures may be maintained on one, some or all ED 201. The collections of PECs, PPS and performance measures may be organized in a common table as records, where each record includes a PEC, a corresponding PPS and a corresponding performance measure. Additionally or alternatively, a subset of records may be associated with a common PEC, where each of the records in the subset includes a different combination of PPS and/or performance measures. For example, multiple ED 201 may have the same PEC, but have different PPS, with each PPS having an associated performance measure. As another example, multiple ED 201 may have the same PEC and the same PPS, but experience different performance measures. The table may track multiple performance measures for a common PEC and PPS. Additionally or alternatively, when multiple ED 201 have a common PEC and PPS, the corresponding performance measures may be merged into a single or subset of records.

At 436, the one or more processors identify a pre-existing configuration from the collection of pre-existing configurations that matches the active ED 201 configuration. The "match" may represent an exact match. Alternatively, a match may be declared when one or more PEC have a select amount of overlap with or similarity to the active ED 201 configuration. For example, when an active ED 201 configuration and/or PEC have 5 separate configuration elements, a match may be declared when at least 3 or 4 of the elements match (or are sufficiently similar) between the active ED 201 configuration and the PEC. Additionally or alternatively, weights may be assigned to the elements, and a weighted score determined by summing the weights for matching elements. A match may be declared when the weight exceeds a threshold. It is recognized that additional or alternative criteria may be used to determine matches.

By way of example, the pre-existing configuration may be identified to be associated with first and second resultant parameter sets in the collection of predefined parameter sets, where the first and second resultant parameter sets have first and second performance measures, respectively. The processors may utilize the performance measures to select one of the first or second resultant parameter sets. For example, when the performance measure represents success rate, the processors may select the PPS based on which of first and second success rates is higher.

At 438, the one or more processors determine one or more resultant parameter sets from the collection of predefined parameter sets based on the pre-existing configuration(s) identified. For example, a single resultant parameter set may be identified as the PPS that corresponds to a single matching PEC. Optionally, the determining operation may include selecting between multiple predefined parameter sets in the collection of predefined parameter sets based on related performance measures (e.g., success rates). For example, when multiple PEC match the active ED 201 configuration, one PPS may be selected that has the best performance measure (e.g., success rate). Alternatively, when multiple PEC correspond to the active ED 201 configuration, the PPS associated with the multiple PEC may be designated as resultant parameter sets. Optionally, when multiple PEC match the active ED 201 configuration, the corresponding PPS may be combined to form a single resultant parameter set or fewer resultant parameter sets. For example, the multiple PPS may be combined through averaging and/or some other mathematical operator.

Optionally, when battery conditions are utilized as a criterion, the processors may determine the one or more PSS from multiple PPS based on the battery condition. For example, two or more PPS may exist for the PEC, with a first PPS associated with a first/normal battery condition and a second PPS associated with a second/low battery condition. As noted above, the request may include a battery condition indication. The processors select one of the first and second PPS based on the battery condition of the IMD 101 and the battery condition associated with the PSS.

At 440, the one or more processors return one or more resultant parameter set (or sets) in connection with the request. The resultant parameter set(s) are utilized by the active ED 201 for bi-directional communication with the IMD 101. The manner in which the request is returned may vary based on the system layout. For example, the CM resource 401 may return the resultant parameter set to the local base station and the local base station re-transmits the resultant parameter set to the ED 201. Additionally or alternatively, the CM resource 401 may transmit the resultant parameter set to the ED 201 through a cellular or other wireless network. Optionally, when the local base station performs the operations of FIG. 4, the local base station may return the resultant parameter set(s) to the ED 201 without intervention (or with limited intervention) by a CM resource 401.

Implantable Medical Device

Figure 5:
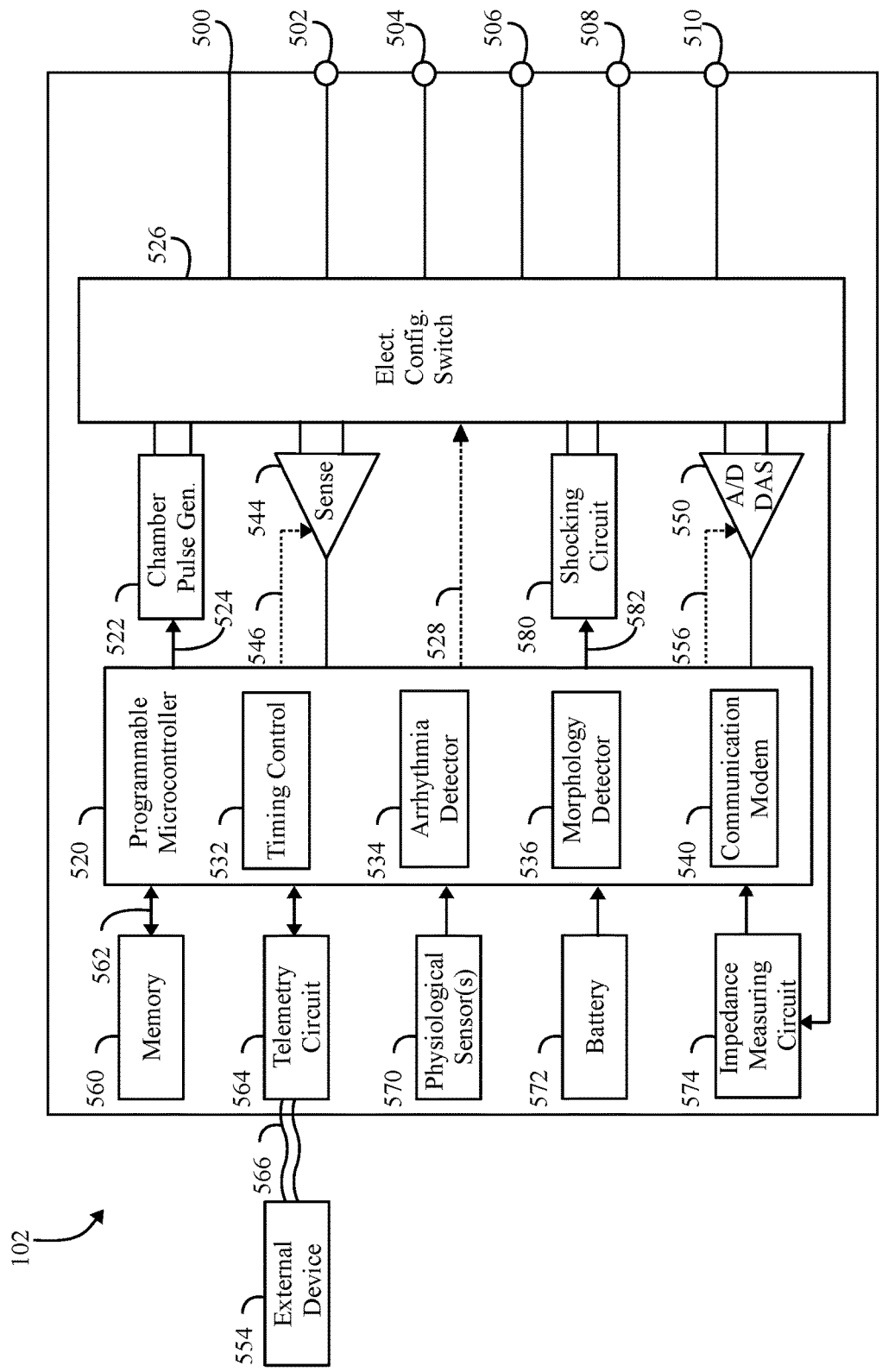
FIG. 5 illustrates a block diagram of exemplary internal components of the IMD in accordance with embodiments herein.

FIG. 5 shows an exemplary IMD 101 that is implanted into the patient as part of the implantable cardiac system. The IMD 101 may be implemented as a full-function biventricular pacemaker, equipped with both atrial and ventricular sensing and pacing circuitry for four chamber sensing and stimulation therapy (including both pacing and shock treatment). Optionally, the IMD 101 may provide full-function cardiac resynchronization therapy. Alternatively, the IMD 101 may be implemented with a reduced set of functions and components. For instance, the IMD may be implemented without ventricular sensing and pacing.

The IMD 101 has a housing 501 to hold the electronic/computing components. The housing 501 (which is often referred to as the "can", "case", "encasing", or "case electrode") may be programmably selected to act as the return electrode for certain stimulus modes. Housing 501 further includes a connector (not shown) with a plurality of terminals 502, 504, 506, 508, and 510. The terminals may be connected to electrodes that are located in various locations within and about the heart. For example, the terminals may include: a terminal 502 to be coupled to an first electrode (e.g., a tip electrode) located in a first chamber; a terminal 504 to be coupled to a second electrode (e.g., tip electrode) located in a second chamber; a terminal 506 to be coupled to an electrode (e.g., ring) located in the first chamber; a terminal 508 to be coupled to an electrode located (e.g., ring electrode) in the second chamber; and a terminal 510 to be coupled to an electrode (e.g., coil) located in the SVC. The type and location of each electrode may vary. For example, the electrodes may include various combinations of ring, tip, coil and shocking electrodes and the like.

The IMD 101 includes a programmable microcontroller 520 that controls various operations of the IMD 101, including cardiac monitoring and stimulation therapy. Microcontroller 520 includes a microprocessor (or equivalent control circuitry), RAM and/or ROM memory, logic and timing circuitry, state machine circuitry, and I/O circuitry.

IMD 101 further includes a first chamber pulse generator 522 that generates stimulation pulses for delivery by one or more electrodes coupled thereto. The pulse generator 522 is controlled by the microcontroller 520 via control signal 524. The pulse generator 522 is coupled to the select electrode(s) via an electrode configuration switch 526, which includes multiple switches for connecting the desired electrodes to the appropriate I/O circuits, thereby facilitating electrode programmability. The switch 526 is controlled by a control signal 528 from the microcontroller 520.

In the example of FIG. 5, a single pulse generator 522 is illustrated. Optionally, the IMD 102 may include multiple pulse generators, similar to pulse generator 522, where each pulse generator is coupled to one or more electrodes and controlled by the microcontroller 520 to deliver select stimulus pulse(s) to the corresponding one or more electrodes.

Microcontroller 520 is illustrated to include timing control circuitry 532 to control the timing of the stimulation pulses (e.g., pacing rate, atrio-ventricular (AV) delay, atrial interconduction (A-A) delay, or ventricular interconduction (V-V) delay, etc.). The timing control circuitry 532 may also be used for the timing of refractory periods, blanking intervals, noise detection windows, evoked response windows, alert intervals, marker channel timing, and so on. Microcontroller 520 also has an arrhythmia detector 534 for detecting arrhythmia conditions and a morphology detector 536 to review and analyze one or more features of the morphology of cardiac signals. Although not shown, the microcontroller 520 may further include other dedicated circuitry and/or firmware/software components that assist in monitoring various conditions of the patient's heart and managing pacing therapies.

The IMD 101 is further equipped with a communication modem (modulator/demodulator) 540 to enable wireless communication with other devices, implanted devices and/or external devices. In one implementation, the communication modem 540 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 540 may be implemented in hardware as part of the microcontroller 520, or as software/firmware instructions programmed into and executed by the microcontroller 520. Alternatively, the modem 540 may reside separately from the microcontroller as a standalone component.

The IMD 101 includes sensing circuitry 544 selectively coupled to one or more electrodes that perform sensing operations, through the switch 526 to detect the presence of cardiac activity in the right chambers of the heart. The sensing circuitry 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD102 to sense low amplitude signal characteristics of atrial fibrillation. Switch 526 determines the sensing polarity of the cardiac signal by selectively closing the appropriate switches. In this way, the clinician may program the sensing polarity independent of the stimulation polarity.

The output of the sensing circuitry 544 is connected to the microcontroller 520 which, in turn, triggers or inhibits the pulse generator 522 in response to the absence or presence of cardiac activity. The sensing circuitry 544 receives a control signal 546 from the microcontroller 520 for purposes of controlling the gain, threshold, polarization charge removal circuitry (not shown), and the timing of any blocking circuitry (not shown) coupled to the inputs of the sensing circuitry.

In the example of FIG. 5, a single sensing circuit 544 is illustrated. Optionally, the IMD 102 may include multiple sensing circuit, similar to sensing circuit 544, where each sensing circuit is coupled to one or more electrodes and controlled by the microcontroller 520 to sense electrical activity detected at the corresponding one or more electrodes. The sensing circuit 544 may operate in a unipolar sensing configuration or in a bipolar sensing configuration.

The IMD 101 further includes an analog-to-digital (ND) data acquisition system (DAS) 550 coupled to one or more electrodes via the switch 526 to sample cardiac signals across any pair of desired electrodes. The data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). The data acquisition system 550 is controlled by a control signal 556 from the microcontroller 520.

The microcontroller 520 is coupled to a memory 560 by a suitable data/address bus 562. The programmable operating parameters used by the microcontroller 520 are stored in memory 560 and used to customize the operation of the IMD 101 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 101 may be non-invasively programmed into the memory 560 through a telemetry circuit 564 in telemetric communication via communication link 566 with the external device 554. The telemetry circuit 564 allows intracardiac electrograms and status information relating to the operation of the IMD 101 (as contained in the microcontroller 520 or memory 560) to be sent to the external device 554 through the established communication link 566.

The IMD 101 can further include magnet detection circuitry (not shown), coupled to the microcontroller 520, to detect when a magnet is placed over the unit. A magnet may be used by a clinician to perform various test functions of the unit 102 and/or to signal the microcontroller 520 that the external programmer 554 is in place to receive or transmit data to the microcontroller 520 through the telemetry circuits 564.

The IMD 101 can further include one or more physiologic sensors 570. Such sensors are commonly referred to as "rate-responsive" sensors because they are typically used to adjust pacing stimulation rates according to the exercise state of the patient. However, the physiological sensor 570 may further be used to detect changes in cardiac output, changes in the physiological condition of the heart, or diurnal changes in activity (e.g., detecting sleep and wake states). Signals generated by the physiological sensors 570 are passed to the microcontroller 520 for analysis. The microcontroller 520 responds by adjusting the various pacing parameters (such as rate, AV Delay, V-V Delay, etc.) at which the atrial and ventricular pacing pulses are administered. While shown as being included within the unit 102, the physiologic sensor(s) 570 may be external to the unit 102, yet still be implanted within or carried by the patient. Examples of physiologic sensors might include sensors that, for example, sense respiration rate, pH of blood, ventricular gradient, activity, position/posture, minute ventilation (MV), and so forth.

A battery 572 provides operating power to all of the components in the IMD 101. The battery 572 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 572 also desirably has a predictable discharge characteristic so that elective replacement time can be detected. As one example, the unit 102 employs lithium/silver vanadium oxide batteries.

The IMD 101 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used.

The IMD 101 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 520 further controls a shocking circuit 580 by way of a control signal 582. The shocking circuit 580 generates shocking pulses of low (e.g., up to 0.5 joules), moderate (e.g., 0.5-10 joules), or high energy (e.g., 511 to 40 joules), as controlled by the microcontroller 520. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

The telemetry circuit 564 is controlled by the microcontroller 560 and receives data for transmission by a control signal. The telemetry circuit 564 allows intra-cardiac electrograms, pressure data, acoustic data, SvO2 data, and status information relating to the operation of IMD 101 (as contained in the microcontroller 520 or memory 560) to be sent through the bi-directional communication link. The telemetry circuit 564 also allows new pacing parameters used by the IMD 101 to be programmed through the bi-directional communication link.

To establish the bi-directional communication link 104 between the external device 201 and the IMD 101, the microcontroller 560 may enter an advertisement mode by instructing the telemetry circuit 564 to transmit or broadcast one or more advertisement notices along a dedicated advertisement channel defined by the wireless protocol. The advertisement channel is a point to multipoint, unidirectional, channel to carry a repeating pattern of system information messages such as network identification, allowable RF channels to establish the bi-directional communication link 104, and/or the like that is included within the advertisement notice. The advertisement notice may be repeatedly transmitted after a set duration or an advertisement period until the bi-directional communication link 104 is established with the external device 201.

External Device

Figure 6:
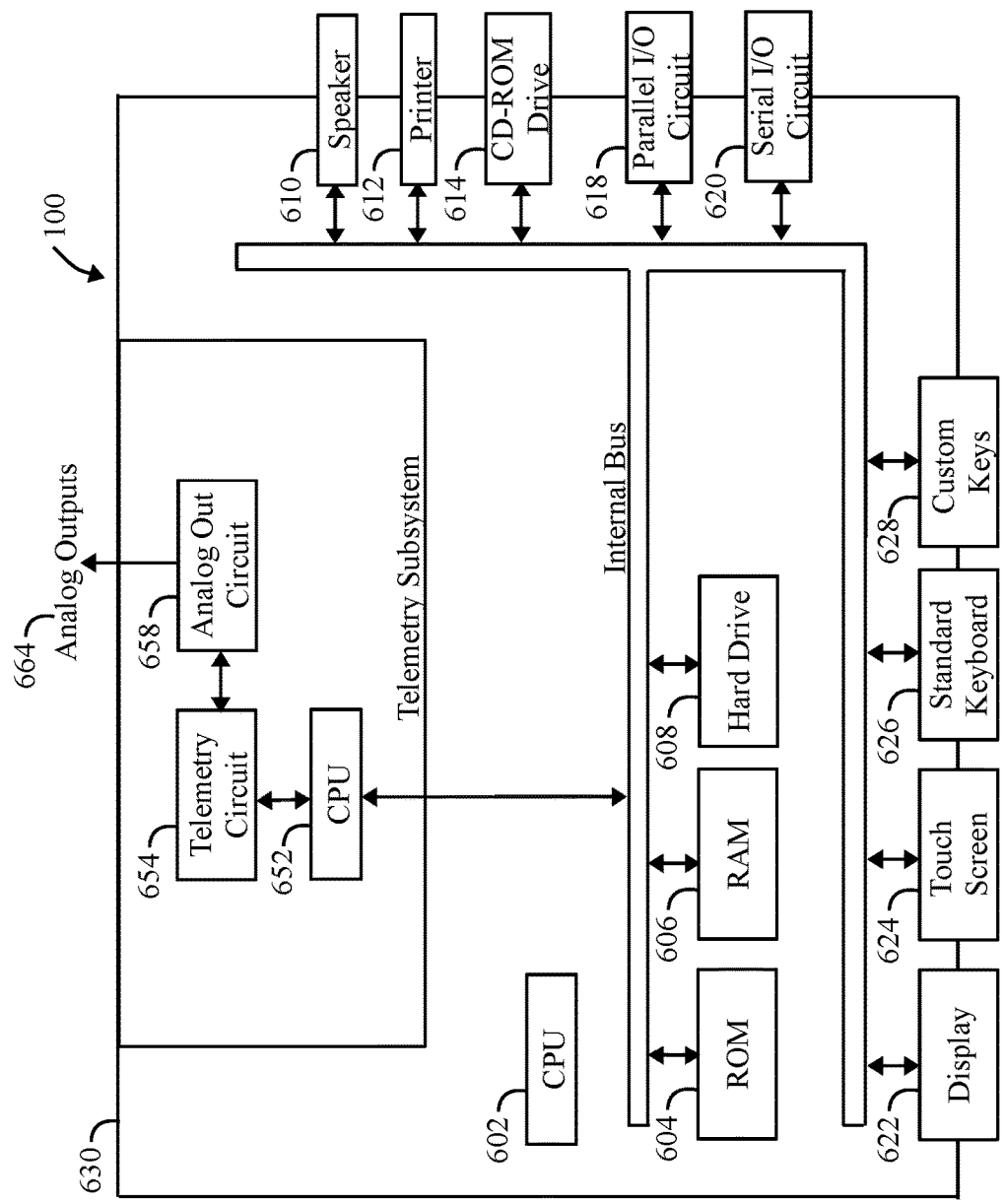
FIG. 6 illustrates a functional block diagram of the external device that is operated in accordance with the processes described herein and to interface with the IMD.

FIG. 6 illustrates a functional block diagram of the external device 201 that is operated in accordance with the processes described herein and to interface with the IMD 101 and communications management resource 401 as described herein. The external device 201 may be a workstation, a portable computer, a tablet computer, an IMD programmer, a PDA, a cell phone, a smart phone and/or the like located within a home of the patient, a hospital or clinic, an automobile, at an office of the patient, or the like. It is recognized that the following discussion in connection with FIG. 6 may describe peripheral accessories connected to an external device that may be optional and omitted.

The external device 201 may include an internal bus that may connect/interface with a Central Processing Unit ("CPU") 602, ROM 604, RAM 606, a hard drive 608, a speaker 610, a printer 612, a CD-ROM drive 614, a parallel I/O circuit 618, a serial I/O circuit 620, the display 622, a touchscreen 624, a standard keyboard 626, custom keys 628, and an RF subsystem 630. The internal bus is an address/data bus that transfers information between the various components described herein. The hard drive 608 may store operational programs as well as data, such as stimulation waveform templates and detection thresholds. Optionally, one or more of the speaker 610, printer 612, CD-ROM drive 614, parallel I/O circuit 618, serial I/O circuit 620, touchscreen 624, standard keyboard 626, and custom keys 628 may be omitted. As a further example, a smart phone would not include a CD-ROM drive 614, a standard keyboard 626 or custom keys 628.

The RAM 606 and/or ROM 604 store one or more applications utilized to manage communication with the IMD 101, local base station 301 and/or CM resource 401, as described herein. The RAM 606 and/or ROM 604 store one or more PEC, PPS and performance measures, as described herein. The CPU 602, CPU 652 and telemetry circuit 654 operate based on the one or more PEC and PPS. The CPU 602, CPU 652 and telemetry circuit 654 operate corporate to collect the performance measures as described herein.

The CPU 602 typically includes a microprocessor, a micro-controller, or equivalent control circuitry, designed specifically to control interfacing with the external device 201 and/or the IMD 101. The CPU 602 may include RAM or ROM memory, logic and timing circuitry, state machine circuitry, and I/O circuitry to interface with the the IMD 101. The display 622 displays various information related to the processes described herein. The touchscreen 624 may display graphic information relating to the IMD 101 and include a graphical user interface. The graphical user interface may include graphical icons, scroll bars, buttons, and the like which may receive or detect user or touch inputs for the external device 201 when selections are made by the user. Optionally the touchscreen 624 may be integrated with the display 622.

The RF subsystem 630 includes a central processing unit (CPU) 652 in electrical communication with a telemetry (RF) circuit 654, which may communicate with the IMD 101 through a bi-directional communications link. The external device 201 may wirelessly communicate with the IMD 101 through various protocols, such as Bluetooth, Bluetooth low energy, ZigBee, MICS, and the like. Optionally, an analog out circuit 658 may be included or omitted.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

The invention claimed is:

1. A computer implemented method for performing a calibration test for communication between an external device (ED) and an implantable medical device (IMD), the method comprising:
configuring the ED with a first parameter set having different parameter values for one or both of data transfer and connectivity parameters;
for a first period of time, repeatedly performing connection attempts between the ED and the IMD utilizing the first parameter set;
determining a connection success rate for establishing connections between the ED and the IMD for the first period of time;
for a second period of time, attempt reading an amount of data from the IMD utilizing the first parameter set;
determining a data transfer rate for the second period of time;
reconfigure the ED with a second parameter set; and
repeating the performing connection attempts, determining, reading, and determining operations using the second parameter set.

2. The method of claim 1, further comprising:
comparing the first and second parameter sets to corresponding thresholds; and
transmitting, to at least one of a local base station or a communications management resource, the first and second parameter sets that satisfy the corresponding thresholds as one or more resultant parameter sets.

3. The method of claim 2, wherein the one or more resultant parameter sets include connectivity parameters and data transfer parameter, along with corresponding performance measures.

4. The method of claim 2, further comprising storing, in memory of the ED, the parameter sets from the first and second parameter sets that satisfy the corresponding thresholds.

5. The method of claim 1, wherein the performing connection attempts further comprises:
recording a connection window in which a connection occurred;
terminating the connection; and
repeating the recording and terminating operations throughout the first period of time.

6. The method of claim 1, wherein the connection success rate indicates a number of successful connections during a connection window.

7. The method of claim 1, wherein multiple connection attempts are performed with the first parameter set and multiple connection attempts are performed with the second parameter set to obtain first and second connection success rates for the first and second parameter sets, respectively.

8. The method of claim 1, wherein the attempt reading the amount of data further comprises:
directing the IMD to transfer an amount of data to the ED, the determining the data transfer rate based on the amount of data transferred.

9. The method of claim 8 wherein the determining the data transfer rate comprises recording at least one of i) a total time utilized to transfer the amount of data, ii) a total number of data packets or frames utilized to transfer the amount of data, iii) a number of errors that occur during transfer of the amount of data, or iv) a retransmitted portion of the amount of data.

10. The method of claim 8, wherein the amount of data represents at least one of i) a prerecorded string of data, ii) pre-recorded calibration related data, iii) electrocardiogram data, iv) episode related data, or v) IMD status data.

11. A system for performing a calibration test between an external device (ED) and an implantable medical device (IMD), the system comprising:
memory to store program instructions;
one or more processors that, when executing the program instructions, are configured to:
configure the ED with a first parameter set having different parameter values for one or both of data transfer and connectivity parameters;
for a first period of time, repeatedly perform connection attempts between the ED and the IMD utilizing the first parameter set;
determine a connection success rate for establishing connections between the ED and the IMD for the first period of time;
for a second period of time, attempt to read an amount of data from the IMD utilizing the first parameter set;
determine a data transfer rate for the second period of time;
reconfigure the ED with a second parameter set; and
repeat the connection attempts, determine, read, and determine operations using the second parameter set.

12. The system of claim 11, wherein the one or more processors are further configured to:
compare the first and second parameter sets to corresponding thresholds; and
transmit, to at least one of a local base station or a communications management resource, the first and second parameter sets that satisfy the corresponding thresholds as one or more resultant parameter sets.

13. The system of claim 11, wherein the one or more resultant parameter sets include connectivity parameters and data transfer parameter, along with corresponding performance measures.

14. The system of claim 11, wherein the one or more processors are further configured to store, in memory of the ED, the parameter sets from the first and second parameter sets that satisfy the corresponding thresholds.

15. The system of claim 11, wherein, in connection with performing the connection attempts, the one or more processors are further configured to:
record a connection window in which a connection occurred;
terminate the connection; and
repeat the record and terminate operations throughout the first period of time.

16. The system of claim 11, wherein the connection success rate indicates a number of successful connections during a connection window.

17. The system of claim 11, wherein multiple connection attempts are performed with the first parameter set and multiple connection attempts are performed with the second parameter set to obtain first and second connection success rates for the first and second parameter sets, respectively.

18. The system of claim 11, wherein, in connection with the attempt to read the amount of data, the one or more processors are further configured to:
direct the IMD to transfer an amount of data to the ED, the data transfer rate determined based on the amount of data transferred.

19. The system of claim 11, wherein, to determine the data transfer rate, the one or more processors are further configured to record at least one of i) a total time utilized to transfer the amount of data, ii) a total number of data packets or frames utilized to transfer the amount of data, iii) a number of errors that occur during transfer of the amount of data, or iv) a retransmitted portion of the amount of data.

20. The system of claim 11, wherein the amount of data represents at least one of i) a prerecorded string of data, ii) pre-recorded calibration related data, iii) electrocardiogram data, iv) episode related data, or v) IMD status data.

* * * * *